United States Patent
Karrer et al.

(10) Patent No.: US 7,635,391 B2
(45) Date of Patent: Dec. 22, 2009

(54) ENDOPROSTHESIS FOR PART OF THE PELVIS

(75) Inventors: David Karrer, Uster (CH); Walter Gross, Ossingen (CH)

(73) Assignee: Zimmer, GmbH, Winterthur (CH)

(*) Notice: Subject to any disclaimer, the term of this patent is extended or adjusted under 35 U.S.C. 154(b) by 0 days.

(21) Appl. No.: 11/046,462

(22) Filed: Jan. 28, 2005

(65) Prior Publication Data

US 2005/0187637 A1 Aug. 25, 2005

(30) Foreign Application Priority Data

Feb. 25, 2004 (EP) ................... 04004256

(51) Int. Cl.
*A61F 2/36* (2006.01)
(52) U.S. Cl. .............................. 623/23.14
(58) Field of Classification Search ... 623/22.11–23.39, 623/18, 19, 22, 11, 16.11, 19.11, 19.12, 19.13, 623/19.14
See application file for complete search history.

(56) References Cited

U.S. PATENT DOCUMENTS

| | | | | |
|---|---|---|---|---|
| 2,641,461 A * | 6/1953 | Lewis | | 266/218 |
| 3,685,058 A * | 8/1972 | Tronzo | | 623/22.15 |
| 3,740,769 A * | 6/1973 | Haboush | | 623/22.36 |
| 3,840,904 A * | 10/1974 | Tronzo | | 623/22.32 |
| 3,903,549 A * | 9/1975 | Deyerle | | 623/22.36 |
| 4,380,090 A * | 4/1983 | Ramos | | 623/22.2 |
| 4,623,352 A * | 11/1986 | Oh | | 623/22.28 |
| 4,662,891 A * | 5/1987 | Noiles | | 623/22.31 |
| 4,792,337 A * | 12/1988 | Müller | | 623/22.36 |
| 4,822,370 A * | 4/1989 | Schelhas | | 623/22.46 |
| 4,842,605 A * | 6/1989 | Sonnerat et al. | | 623/22.45 |
| 4,883,489 A * | 11/1989 | Grundei et al. | | 623/22.36 |
| 4,936,856 A * | 6/1990 | Keller | | 623/22.36 |
| 4,955,919 A * | 9/1990 | Pappas et al. | | 623/22.26 |
| 5,108,445 A * | 4/1992 | Ashby | | 623/22.29 |
| 5,176,711 A * | 1/1993 | Grimes | | 623/22.22 |
| 5,192,329 A * | 3/1993 | Christie et al. | | 623/22.22 |
| 5,314,490 A * | 5/1994 | Wagner et al. | | 623/22.36 |
| 5,326,368 A * | 7/1994 | Collazo | | 623/22.22 |
| 5,370,704 A * | 12/1994 | DeCarlo, Jr. | | 623/22.22 |
| 5,425,778 A * | 6/1995 | Zichner et al. | | 623/22.29 |
| 5,507,825 A * | 4/1996 | Frei | | 623/22.36 |
| 5,507,827 A * | 4/1996 | Grundei et al. | | 623/22.35 |
| 5,624,464 A * | 4/1997 | Wagner et al. | | 623/22.27 |
| 5,702,477 A * | 12/1997 | Capello et al. | | 623/22.21 |

(Continued)

FOREIGN PATENT DOCUMENTS

DE 4133433 C1 * 5/1993

(Continued)

*Primary Examiner*—David J Isabella
*Assistant Examiner*—Ann Schillinger
(74) *Attorney, Agent, or Firm*—Baker & Daniels LLP

(57) ABSTRACT

The invention relates to an endoprosthesis for part of the pelvis having at least one base element which can be secured to a resected iliac bone and at least one hip shell attachable at a spacing thereto, with the base element having a first neck which in particular projects at an angle α from the orthogonal to a planar connection surface and the hip shell having a second neck which in particular projects at an angle β from its polar axis, with at least one separate intermediate element being provided which can be installed between the first neck and the second neck.

23 Claims, 5 Drawing Sheets

U.S. PATENT DOCUMENTS

| | | | |
|---|---|---|---|
| 5,800,557 A * | 9/1998 | Elhami | 623/23.12 |
| 5,800,558 A * | 9/1998 | LaHaise, Sr. | 623/22.2 |
| 5,871,548 A * | 2/1999 | Sanders et al. | 623/22.36 |
| 5,916,268 A * | 6/1999 | Schollner et al. | 623/22.36 |
| 5,928,288 A * | 7/1999 | Wilson | 623/22.22 |
| 6,120,540 A * | 9/2000 | Apple et al. | 623/11.11 |
| 6,273,891 B1 * | 8/2001 | Masini | 606/91 |
| 6,423,097 B2 * | 7/2002 | Rauscher | 623/21.16 |
| 6,589,284 B1 * | 7/2003 | Silberer | 623/22.29 |
| 6,926,740 B2 * | 8/2005 | Lewis et al. | 623/22.28 |
| 2003/0050703 A1 * | 3/2003 | Harris et al. | 623/22.2 |
| 2004/0199257 A1 * | 10/2004 | Dooney | 623/22.24 |
| 2005/0071014 A1 * | 3/2005 | Barnett et al. | 623/19.14 |
| 2007/0043448 A1 * | 2/2007 | Murray | 623/22.46 |

FOREIGN PATENT DOCUMENTS

| | | |
|---|---|---|
| EP | 0628294 A1 | 12/1994 |
| WO | WO 88/01491 A1 | 3/1988 |

* cited by examiner

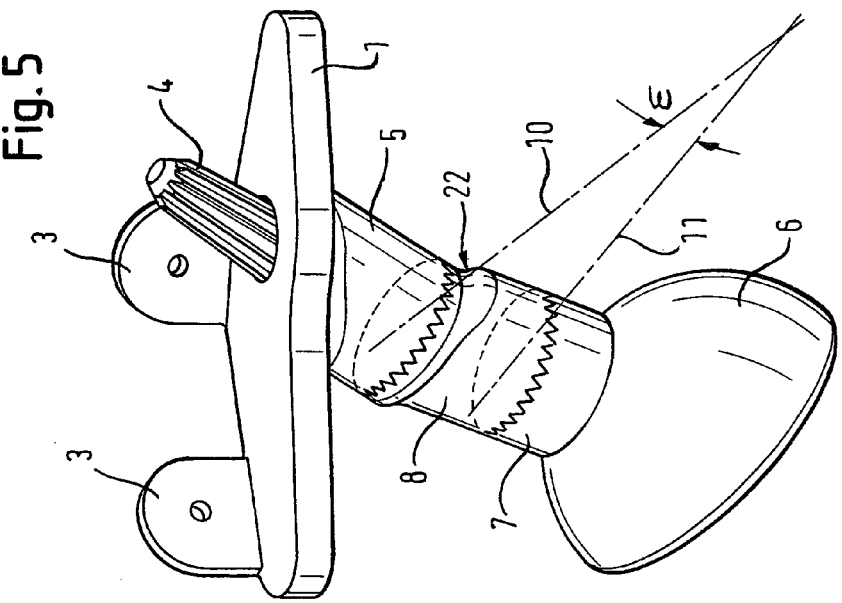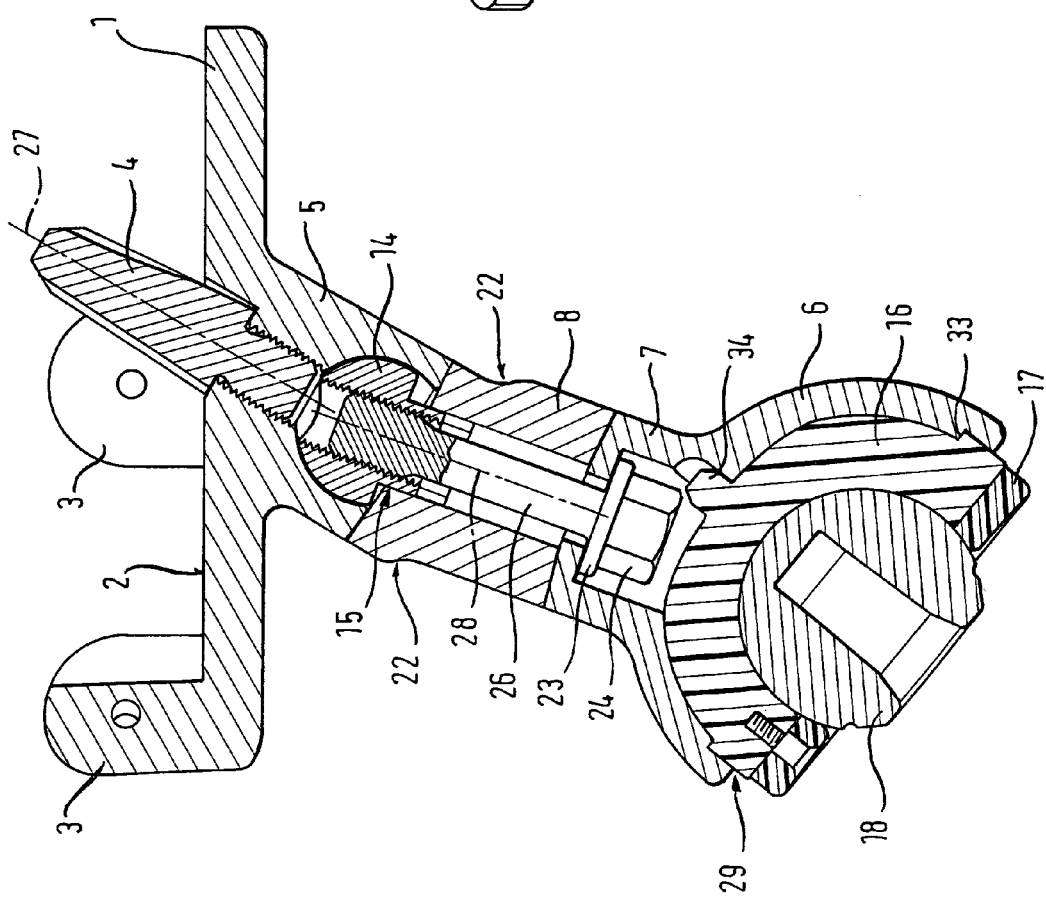

ENDOPROSTHESIS FOR PART OF THE PELVIS

BACKGROUND OF THE INVENTION

The invention relates to an endoprosthesis for part of the pelvis having at least one base element which can be secured to a resected iliac bone and at least one hip shell attachable at a spacing thereto, with the base element having a first neck which in particular projects at an angle α from the orthogonal to a planar connection surface and the hip shell having a second neck which in particular projects at an angle β from its polar axis.

There are some tumor patients where the ilium, i.e. half the pelvic bone, has to be resected from below by one-third to two-thirds of its height. Without further aid measures, it was previously customary to amputate the associated leg in order to avoid complications due to a lack of attachment to the trunk. To avoid such amputations, endoprostheses for part of the pelvis have been developed which may not be put under excessive strain, but which exert at least a passive retainer function for the leg attached to it.

Such an endoprosthesis is shown in the patent application WO 88/01491 in which two necks are molded to a hip shell and each have a receiving bore for a spigot with a self-locking fixed fit. The spigots are each anchored at their other end to the resected ilium or pubic bone. The anchoring to the ilium in this process takes place via a plate-shaped base element.

A further endoprosthesis of this kind is known from the patent application EP 0 628 294 A1. Receiving bores for spigots having a self-locking fit are provided at a neck of a hip shell. The securing of a shaft part continuing the spigot takes place by intramedullary engagement into a groove milled into the stub of the ilium. A mechanical adjustment unit is additionally provided with the aid of which the shaft part can be adjusted in an elongate bore of a base element secured to the ilium.

It is, however, a disadvantage with the aforesaid endoprosthesis for part of the pelvis that the length of the spigot and the angular position of the spigot are fixedly predetermined relative to the base element and thus also the position and the alignment of the hip shell. The desired position of the hip bone must therefore already be taken into account on the resection of the iliac bone with respect to the height and direction of the resection incision.

SUMMARY OF THE INVENTION

It is therefore an underlying object of the present invention to provide an endoprosthesis for part of the pelvis of the initially named kind which is characterized by a design which is as simple as possible with simultaneously increased flexibility with respect to the positioning and/or alignment of the hip shell.

This object is satisfied in that at least one separate intermediate element is provided which can be installed between the first neck and the second neck.

Provision is made in the endoprosthesis for part of the pelvis in accordance with the invention for a further component to be installable between the neck of the base element and the neck of the hip shell. Increased flexibility of the endoprosthesis for part of the pelvis is ensured by the possibility of installing a separate intermediate element. This flexibility is in particular of advantage when the surgeon finds conditions during the surgical procedure which require a resection incision different from the original surgery plan.

Different relative positions between the base element and the hip shell can preferably be realized by means of the intermediate element. This in particular makes it possible for repositioning of the hip shell even after the anchoring of the base part to the iliac bone.

It is particularly advantageous for at least two intermediate elements to be provided which differ from one another and which can each be installed between the first neck and the second neck. The endoprosthesis for part of the pelvis in accordance with the invention hereby provides a kit of different intermediate elements which can be installed alternatively to one another between the first neck of the base element and the second neck of the hip shell. The surgeon inserting the endoprosthesis for part of the pelvis can choose that intermediate element from a set of intermediate elements differing from one another which permits the desired position for the hip shell most favorable for the respective patient.

Intermediate elements of different lengths are preferably provided so that the spacing between the base element and the hip shell, and thus the spacing between the resected stub of the ilium and the joint ball of the femur, can be varied.

Additionally or alternatively, at least one intermediate element can be cranked so that the center axes of the first neck and of the second neck can be tilted toward one another or can run in a parallel offset manner. Further relative positions are hereby made possible between the base element and the hip shell which cannot be realized by a mere extension by means of a straight intermediate element.

Provision can furthermore be made in accordance with the invention for the intermediate element and the first and second necks each to be provided in contact areas with projections and recesses latchable at different angular positions. The projections and recesses in the contact areas can in particular correspond to a toothed Hirth coupling. It is hereby achieved, in particular when a cranked intermediate element and/or a hip shell not rotationally symmetrical with respect to its polar axis is used, that the latter, in particular its polar axis, can be oriented in different spatial directions so that further relative positions can in turn be realized between the base element and the hip shell. The projections and recesses additionally represent security against rotation.

Furthermore, contact planes of at least one intermediate element and defined by contact areas can stand at an angle ε to one another, in particular an acute angle, different from zero. In particular, contact planes standing at an angle ε to one another can be provided only with cranked intermediate elements. It is hereby made possible for cranked intermediate elements to be used alternatively to non-cranked intermediate elements whose contact planes extend parallel to one another.

In a particularly preferred embodiment, the intermediate element can be spanned between the first neck and the second neck via a draw rod. A particularly firm and secure connection can hereby be achieved between the intermediate element and the base element or the hip shell. The draw rod in this process can in particular be guided inside the respective intermediate element, made for example as a sleeve, and the two ends of the draw rod can be anchored in the base element and the hip shell.

Draw rods which match intermediate elements of different lengths are preferably provided.

It is furthermore proposed in accordance with the invention that a waisted bolt is provided as the draw rod.

The draw rod can engage into a head held in the first neck. The head can in particular be made as a ball joint. It can hereby be achieved that the head held in the first neck can cooperate both with non-cranked and cranked intermediate elements, in particular with differently cranked intermediate elements.

It is furthermore preferred for the head to be secured against rotation with respect to the intermediate element via a shape-matched plug-in connection. This is in particular of advantage when the head can be released from its holding in the first neck in a position achievable by rotation.

In a further preferred embodiment, the head has a spherical surface over an angular range $\gamma$ of more than 180°, in particular of more than 200°, the spherical surface having a flattened section formed in the shape of a band extending beyond the pole, with the head being able to be inserted into a cavity formed in the first neck in an installation position rotated by 90° with respect to the functional position.

Differently sized anchoring spigots can be inserted into the base element to secure the base element to the iliac bone in order to anchor the endoprosthesis for part of the pelvis to the stub of the iliac bone so that a matching anchoring spigot can be selected in dependence on the respective anatomical demands.

An inner shell can furthermore be insertable into the hip shell with a snap connection. In particular a joint ball can be inserted into the hip shell together with an inner shell which surrounds the joint ball by more than 180° so that a femur can be secured to the endoprosthesis for part of the pelvis.

To achieve a particularly simple and effective holding of the joint ball, the inner shell can have a holding ring which can be secured to the hip shell after the insertion of a joint ball.

Base elements, hip shells and intermediate elements can be provided as parts of a trial kit which each consist of a plastic, which can be sterilized, and which serve for the location of a matching spatial position of the hip shell relative to the base element, with the trial hip shells each having a contact area matching to a joint ball so that an inner shell can be dispensed with.

The prosthesis parts for trial prostheses and for finally insertable prostheses can be characterized differently to prevent possible confusion. The engagement positions of intermediate elements and first and second noses can each be marked so that the matching spatial position of the hip shell determined by means of the components of the endoprosthesis for part of the pelvis consisting of plastic can easily be transferred to the finally insertable prostheses.

The invention will be further described in the following by way of example with reference to the drawings.

BRIEF DESCRIPTION OF THE DRAWINGS

FIG. 5 is a perspective view of an endoprosthesis for part of the pelvis in accordance with the invention with a cranked sleeve;

FIG. 6 is an enlarged longitudinal section through the arrangement in FIG. 5 with inserted inner shell and joint ball;

DESCRIPTION OF THE PREFERRED EMBODIMENTS

Figure 1:
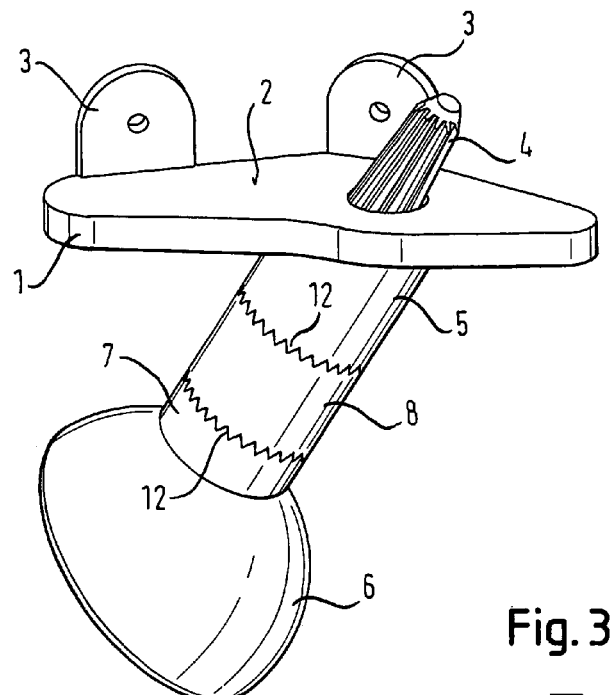
FIGS. 1 to 3 show different views of an endoprosthesis for part of the pelvis in accordance with the invention with a straight sleeve.
Figure 2:
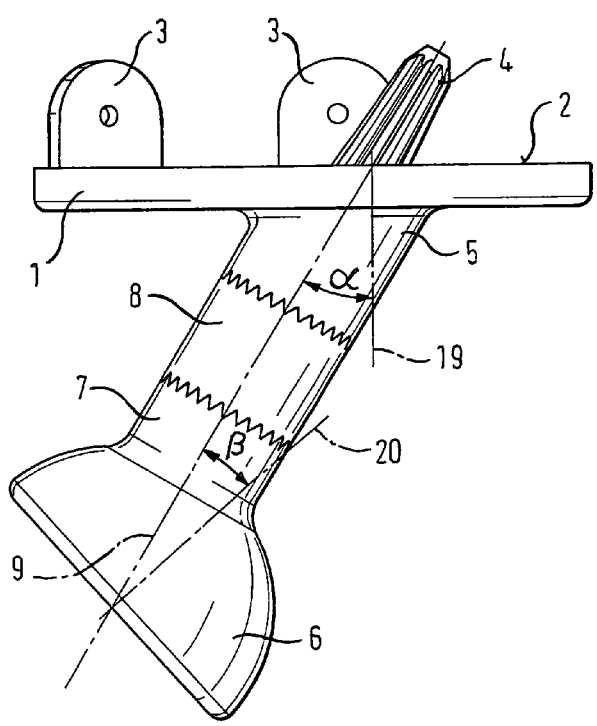
Figure 3:
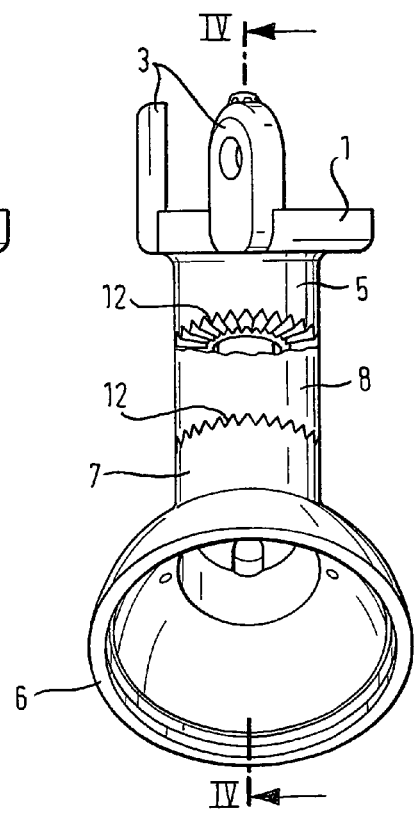

FIGS. 1, 2 and 3 show different views of an endoprosthesis for part of the pelvis in accordance with the invention shown in the assembled state for the replacement of a part of the pelvis in the region of the hip joint having a base element 1 which can be secured to a resected iliac bone, a hip shell 6 for the receiving of a hip joint ball and an intermediate element which is designed as a sleeve 8 and is arranged between the base element 1 and the hip shell 6.

A planar surface 2 of the base element 1 contacts the resection plane of the resected iliac bone (not shown). An anchoring spigot 4, which engages into a bore provided in the stub of the iliac bone, is inserted into the base element 1 to secure the base element 1 to the iliac bone.

The anchoring spigot 4 is inclined by an angle $\alpha$ with respect to an orthogonal 19 to the connection surface 2. The anchoring spigot 4 tapers conically at its end projecting beyond the connection surface 2 in the direction of the iliac bone and has a surface with elongate ribs.

In addition to the anchoring spigot 4, two bracket pieces 3 are provided for the securing of the base element 1 to the iliac bone and are connected to the base element 1 in a marginal region thereof, and each project from the connection surface 2 of the base element 1 at an angle of 90°. The bracket pieces 3 can each be secured to the iliac bone via a passage bore.

The base element 1 furthermore has a first neck 5 likewise projecting from the orthogonal 19 to the planar connection surface 2 at the angle $\alpha$ so that the inclinations of the first neck 5 and of the anchoring spigot 4 opposite the orthogonal 19 to the planar connection surface 2 correspond to one another.

The first neck 5 of the base element 1 is connected to a second neck 7 of the spherically shaped hip shell 6 via the cylindrically shaped sleeve 8. The respective central axes of the anchoring spigot 4, of the first neck 5, of the sleeve 8 and of the second neck 7 form a common central axis 9 in FIGS. 1, 2 and 3. The second neck 7 is inclined by an angle $\beta$ with respect to the polar axis 20 of the hip shell 6.

The sleeve 8 and the first and second necks 5, 7 are each provided with projections and recesses 12 on their contact areas lying opposite one another, said projections and recesses being designed in the manner of a toothed Hirth coupling so that different angular positions of the sleeve 8 with respect to the central axis 9 are possible with respect to the first neck 5 and to the second neck 7 with respect to the sleeve 8.

Figure 4:
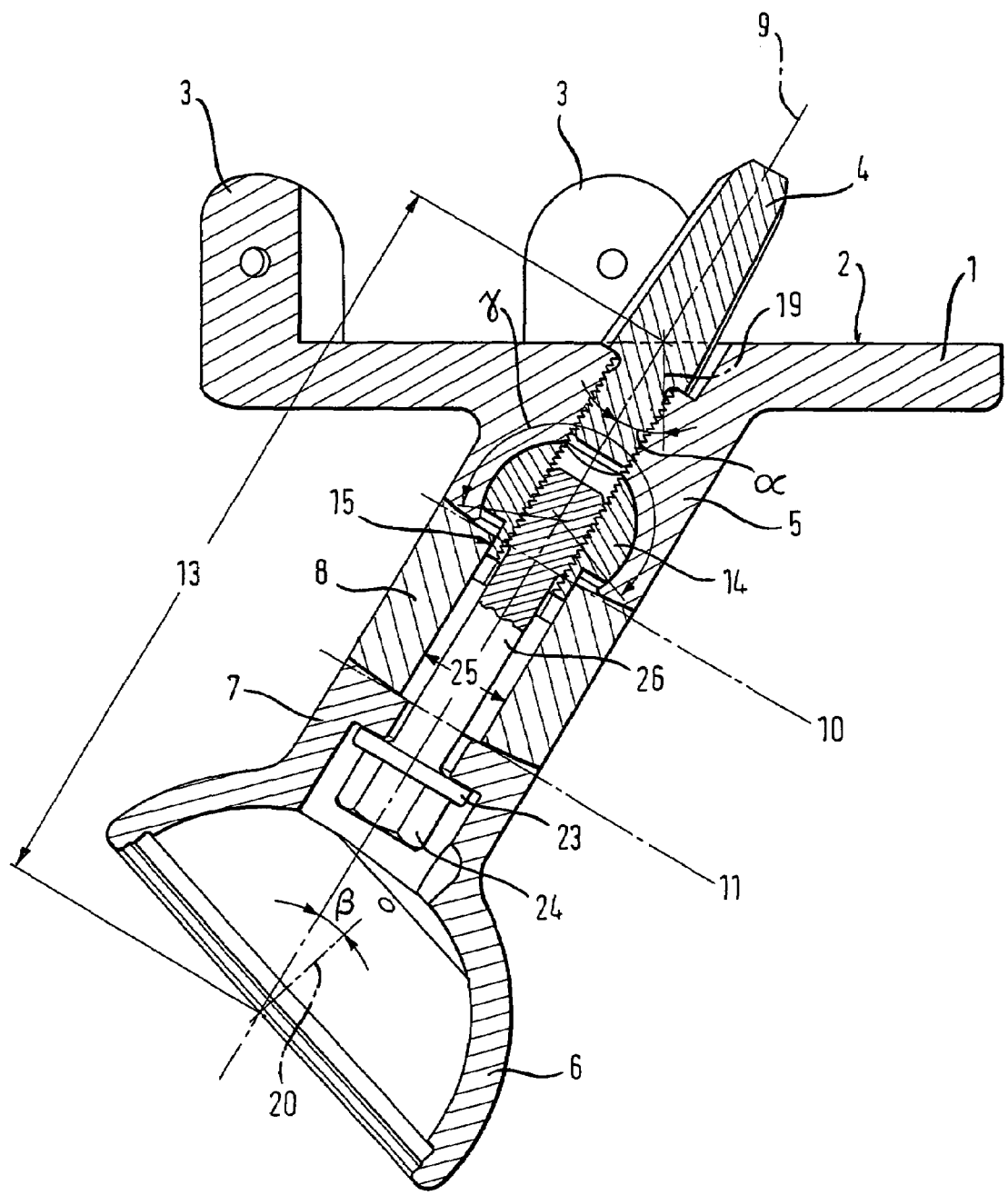
FIG. 4 is an enlarged longitudinal section through the arrangement in FIG. 3.

FIG. 4 shows a cross-section of the endoprosthesis for part of the pelvis in accordance with the invention along the line IV-IV in FIG. 3. For reasons of simplicity, the representation of the projections and recesses 12 has been omitted in FIG. 4. It can be seen from FIG. 4 that the contact areas of the first neck 5, of the sleeve 8 and of the second neck 7 are each made approximately planar. The contact planes 10, 11 defined by the contact areas in the assembled state of the endoprosthesis for part of the pelvis are aligned parallel to one another.

It can furthermore be seen from FIG. 4 that the anchoring spigot 4 inserted into the base element 1 extends up to and into the first neck 5 of the base element 1 and is screwed into the base element 1. In the first neck 5 of the base element 1, a cavity is furthermore formed in which a spherical head 14 is held which will be explained in more detail in another passage and has a spherical surface over an angular region $\gamma$ of 200° and which is secured against rotation with respect to the sleeve 8 via a shape-matched plug-in connection 15.

An elongate waisted bolt 26, which serves as a draw rod and clamps the sleeve 8 between the first neck 5 and the second neck 7, engages into the spherical head 14 held in the first neck 5. The part of the waisted bolt 26 not screwed into the spherical head 14 is arranged within the sleeve 8 or within a bore of the second neck 7 of the hip shell 6. The sleeves 8 have a clearance 25 which is larger than the diameter of the waisted bolt 26.

The head of the waisted bolt 26 is made as a hexagon 24 to permit the screwing of the waisted bolt 26 into the spherical head 14 held in the first neck 5. The waisted bolt 26 furthermore includes a collar 23 which, in the assembled state of the endoprosthesis for part of the pelvis, is held in a cavity of the second neck 7 connected to the bore so that the sleeve 8 is clamped between the first neck 5 and the second neck 7.

The spacing 13 between the base element 1 and the hip shell 6 can be varied in that sleeves 8 of different lengths and waisted bolts 26 of matching lengths thereto are provided which can each be installed or screwed between the first neck 5 and the second neck 7.

FIGS. 5 and 6 show an embodiment of an endoprosthesis for part of the pelvis in accordance with the invention with a cranked sleeve 8, with respectively the same or corresponding parts being designated with the same reference numerals so that a repeat representation is dispensed with and only the differences of the embodiment shown in these Figures with respect to the first embodiment are explained.

In accordance with FIGS. 5 and 6, the sleeve 8 is cranked or bent like a hook. The crank 22 of the sleeve 8 has the consequence that the contact planes 10, 11 defined by the contact areas stand at an acute angle ε to one another. A common central axis 27 of the anchoring spigot 4 and of the first neck 5 is inclined with respect to a common central axis 28 of the waisted bolt 26, of the larger part of the sleeve 8 and of the second neck 7. Due to the engagement of the waisted bolt 26, the spherical head 14 shown in FIG. 6 is tilted with respect to the spherical head shown in FIG. 4.

An inner shell 16 likewise made in spherical shape is inserted into the hip shell 6, with the two shells 6, 16 each having a shoulder 33 being connected to one another by means of a snap connection 29. The inner shell 16 surrounds a joint ball 18, in particular an artificial joint ball, by more than 180° in this process. The inner shell 16 includes for this purpose a holding ring 17 which, after the insertion of the joint ball 18 into the inner shell 16, is connected to the latter.

To ensure a correct relative positioning of the inner shell 16 with respect to the hip shell 6, the inner shell 16 has a nose 34 in its polar region which projects in the direction of the hip shell 6 and engages, in the assembled state of the endoprosthesis for part of the pelvis, into a cut-out of the hip shell 6 continuing the cavity of the second neck 7.

Figure 8:
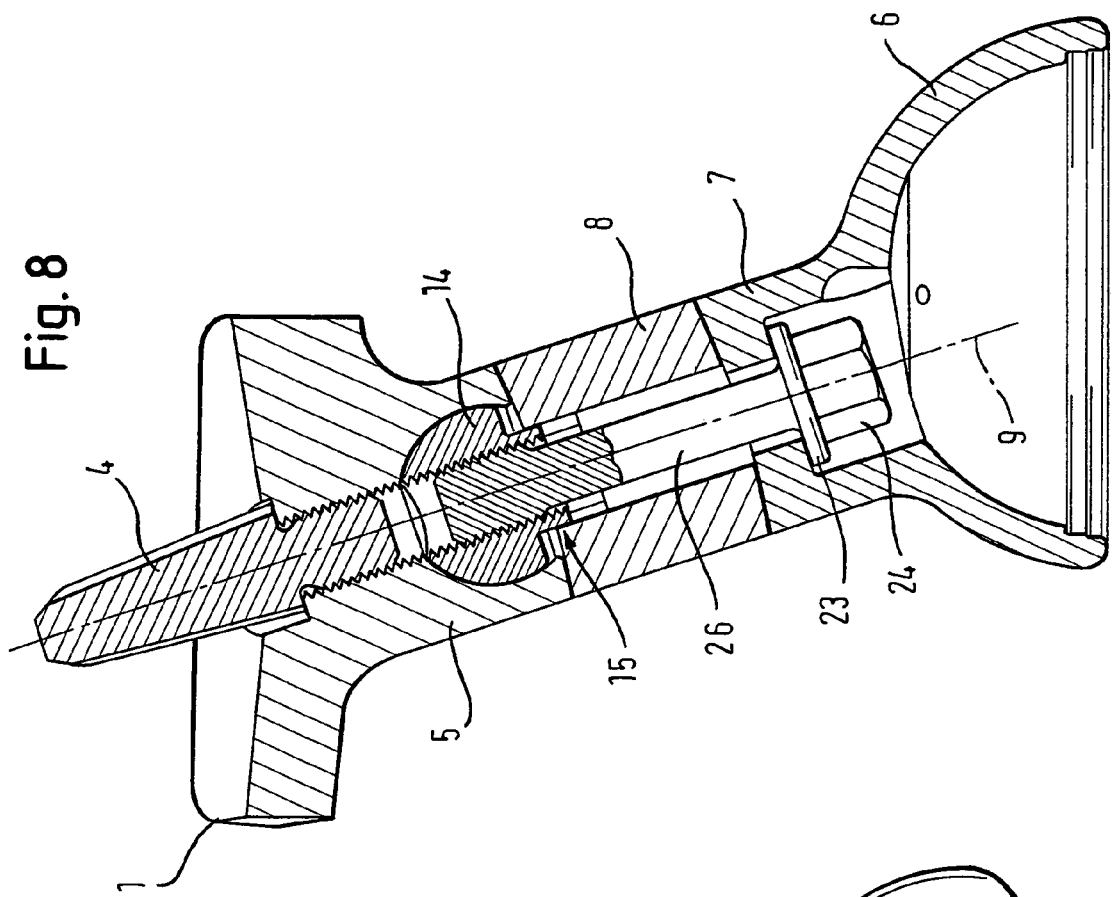
FIG. 8 is an enlarged longitudinal section through the arrangement in FIG. 7.
Figure 7:
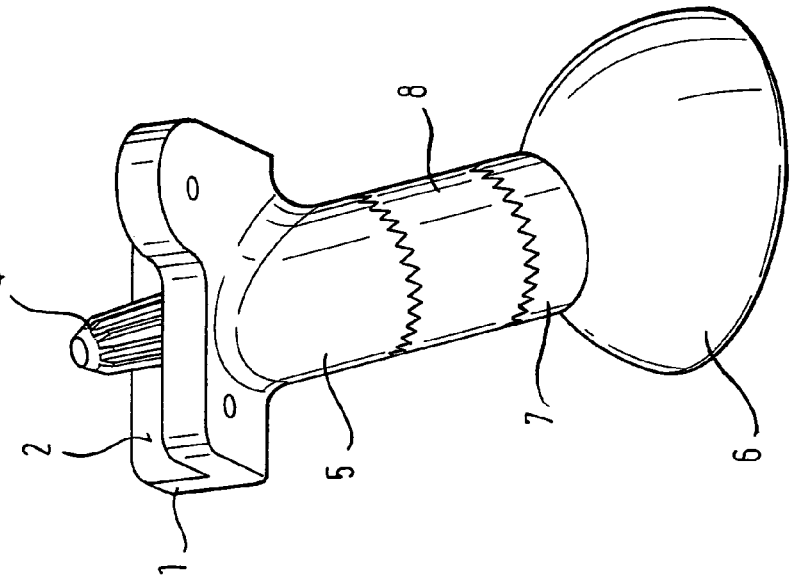
FIG. 7 is a perspective view of an endoprosthesis for part of the pelvis in accordance with the invention with a straight sleeve and a bracket-shaped connection surface directly applicable to the sacrum.
Figure 9:
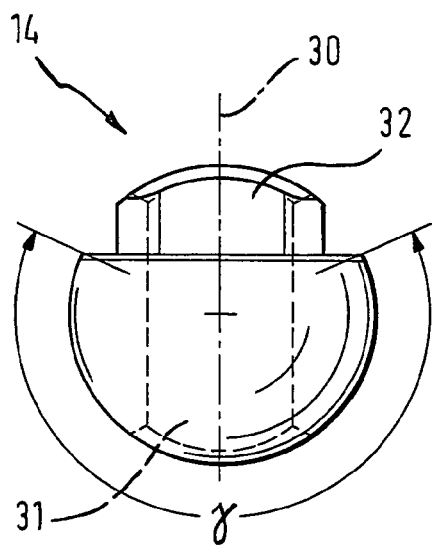
FIGS. 9 to 12 show different views of a ball joint of an endoprosthesis for part of the pelvis in accordance with the invention.
Figure 10:
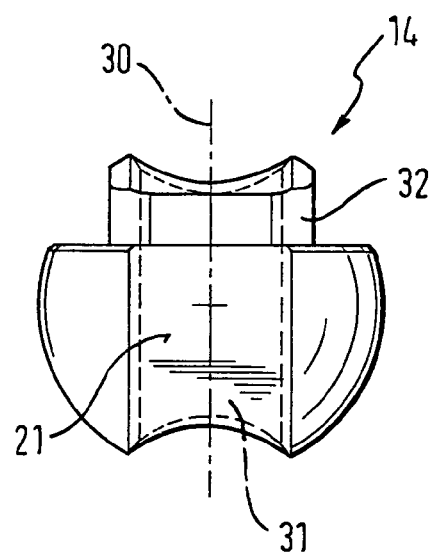
Figure 11:
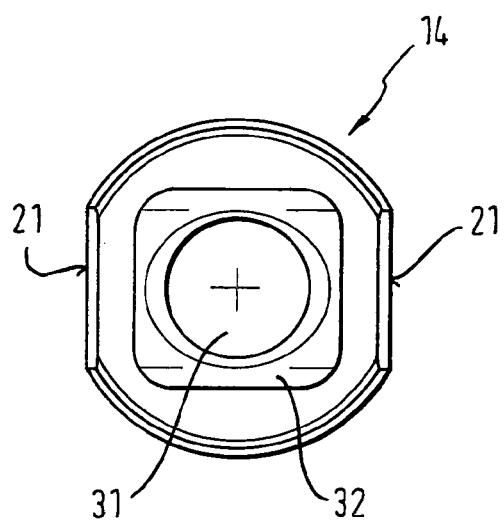
Figure 12:
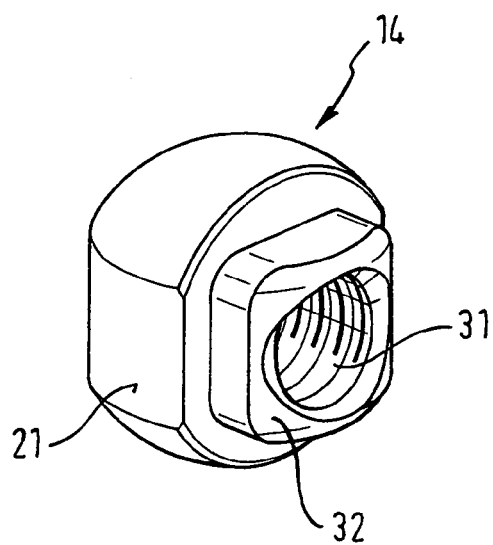

FIGS. 7 and 8 show a further embodiment of an endoprosthesis for part of the pelvis in accordance with the invention which differs from the two aforesaid embodiments in particular by the design of the base element 1. To permit application directly at the sacrum, the endoprosthesis for part of the pelvis in accordance with FIGS. 7 and 8 has a bracket-shaped connection surface 2.

FIGS. 9, 10, 11 and 12 show different views of the spherical head 14 already mentioned above. The spherical head 14 has a spherical base shape with a spherical surface extending over an angular range γ of 200°. The spherical head furthermore has a continuous threaded bore 31 which is formed along the polar axis 30 of the spherical head 14 and into which the waisted bolt 26 engages in the assembled state of the endoprosthesis for part of the pelvis.

A plug projection 32 through which the bore 31 passes is formed at the side of the spherical head 14 remote from the pole. The plug projection 32 is made substantially square in planes extending to the polar axis 30, with the plug projection 32, in the assembled state of the endoprosthesis for part of the pelvis, projecting into the correspondingly shaped passage of the sleeve 8 so that the spherical head 14 is secured against rotation.

The spherical surface of the spherical head 14 has a flattened section made in the shape of a band 21 extending beyond the pole. The spherical head 14 thus has a circular shape—interrupted by two oppositely disposed flattened sides—in planes extending perpendicular to the polar axis 30. The inlet opening of the cavity of the first neck 5 has a corresponding shape so that the spherical head 14 inserted into the cavity can be held in the first neck 5 in a functional position rotated through 90° with respect to the installation position.

The assembly of an endoprosthesis for part of the pelvis in accordance with the invention will be described in the following with reference to the Figures.

The base element 1 is first secured to the resected iliac bone by means of the anchoring spigot 4 and of the two bracket pieces 3 so that the connection area 2 of the base element 1 contacts the stub of the ilium. The spherical head 14 has already been inserted into the cavity of the first neck 5 before the attachment of the base element 1 to the stub of the ilium, but can alternatively also only be inserted after the attachment of the base element 1.

The surgeon then selects that sleeve 8 from a set of sleeves 8, which differ from one another and which permit different relative positions between the base element 1 and the hip shell 6, which permits the most expedient relative position under anatomical aspects. The sleeves 8 can have different lengths and/or be cranked.

Subsequently, a waisted bolt 26 matching the length of the selected sleeve 8 is selected from a set of waisted bolts of different lengths. The waisted bolt 26 is then led through the bore formed in the second neck 7 of the hip shell 6 and through the sleeve 8 and is screwed into the bore 31 of the spherical head 14 held in the first neck 5.

The waisted bolt 26 is tightened while taking into account the orientation of the hip shell 6, and optionally the crank 22 of the sleeve 8, so that the projections and recesses 12 of the contact areas of the first neck 5, of the sleeve 8 and of the second neck 7 engage into one another. The plug projection 32 of the spherical head 14 engages into the interior of the sleeve 8 so that a shape-matched plug-in connection 15 secured against rotation is formed with respect to the sleeve. When a cranked sleeve 8 is used, the spherical head 14 is tilted accordingly due to the engagement of the waisted bolt 26 (FIG. 6).

The inner shell 16 is finally inserted into the hip shell 6 and is secured thereto by means of the snap connection 29 (FIG. 6). The joint ball 18 held in the inner shell 16 by the holding ring 17 was previously inserted into the inner shell 16, with the inner shell 16 including the holding ring 17 surrounding the joint ball 18 by more than 180°.

An endoprosthesis for part of the pelvis in accordance with the invention thus has increased flexibility with respect to the positioning and alignment of the hip shell 6 due to the available intermediate elements 8, which are in particular of different lengths and/or cranked, so that the relative position between the base element 1 and the hip shell 6 can be achieved during a surgical treatment which is respectively most expedient for anatomical reasons. In particular greater degrees of freedom are made possible for the surgeon on the setting of the resection incision at the iliac bone.

The invention claimed is:

1. An endoprosthesis for part of the pelvis comprising at least one base element which can be secured to a resected iliac bone and at least one hip shell attachable at a spacing thereto, the hip shell configured to replicate a portion of the pelvis and articulate with a femoral head, the base element having a first neck which projects at an angle α from the orthogonal to a planar connection surface and the hip shell having a second neck which projects at an angle β from its polar axis, each of the first neck and the second neck having an opening formed therein;

at least one separate intermediate element having a bore extending therethrough, wherein the intermediate element is adapted to be installed between and secured to the first neck and the second neck by aligning at least a portion of the bore of the intermediate element with the openings in each of the first neck and the second neck; and a connection mechanism comprising a draw rod and a rotatable head, the rotatable head rotatably secured to the first neck, the draw rod received within the opening in the second neck and extending through the bore in the intermediate element and through the opening in the first neck to secure the draw rod to the rotatable head, whereby the connection mechanism secures the intermediate element to both of the first neck and the second neck.

2. The endoprosthesis for part of the pelvis in accordance with claim 1, wherein that at least two intermediate elements are provided which differ from one another and which can each be installed between the first neck and the second neck.

3. The endoprosthesis for part of the pelvis in accordance with claim 1, wherein intermediate elements of different lengths are provided.

4. The endoprosthesis for part of the pelvis in accordance with claim 1, wherein at least one intermediate element is cranked.

5. The endoprosthesis for part of the pelvis in accordance with claim 1, wherein the intermediate element and the first and second necks are each provided in contact areas with projections and recesses latchable at different angular positions.

6. The endoprosthesis for part of the pelvis in accordance with claim 5, wherein the projections and recesses in the contact areas correspond to a toothed Hirth coupling.

7. The endoprosthesis for part of the pelvis in accordance with claim 1, including contact planes of at least one intermediate element and defined by contact areas stand at an angle to one another, in particular an acute angle ε, different from zero.

8. The endoprosthesis for part of the pelvis in accordance with claim 1, wherein matching draw rods are provided for intermediate elements of different lengths.

9. The endoprosthesis for part of the pelvis in accordance with claim 1, wherein a waisted bolt is provided as the draw rod.

10. The endoprosthesis for part of the pelvis in accordance with claim 1, wherein the rotatable head is made as a ball joint.

11. The endoprosthesis for part of the pelvis in accordance with claim 1, wherein the rotatable head is secured against rotation with respect to the intermediate element via a shape-matched plug-in connection.

12. The endoprosthesis for part of the pelvis in accordance with claim 1, wherein the rotatable head has a spherical surface over an angular range γ of more than 180° the spherical surface having a flattened section shaped in the form of a band extending beyond the pole, with the rotatable head being able to be inserted into a cavity formed in the first neck in an installation position rotated by 90° with respect to a functional position.

13. The endoprosthesis for part of the pelvis in accordance with claim 1, wherein differently sized anchoring spigots can be inserted into the base element for the securing of the base element to the iliac bone.

14. The endoprosthesis for part of the pelvis in accordance with claim 1, wherein an inner shell can be inserted into the hip shell with a snap connection.

15. The endoprosthesis for part of the pelvis in accordance with claim 14, wherein the inner shell has a holding ring which can be secured to the hip shell after the insertion of a joint ball.

16. The endoprosthesis for part of the pelvis in accordance with claim 1, wherein a joint ball can be inserted into the hip shell together with an inner shell which surrounds the joint ball by more than 180°.

17. The endoprosthesis for part of the pelvis in accordance with claim 1, wherein base elements, hip shells and intermediate elements can be provided as parts of a trial kit which each consist of a plastic, which can be sterilized, and which serve for the location of a matching spatial position of the hip shell relative to the base element, with the trial hip shells each having a contact area matching a joint ball.

18. The endoprosthesis for part of the pelvis in accordance with claim 17, wherein the prosthesis parts for trial prostheses and for finally insertable prostheses are characterized differently.

19. The endoprosthesis for part of the pelvis in accordance with claim 17, wherein the engagement positions of intermediate elements and of first and second necks are respectively marked.

20. The endoprosthesis for part of the pelvis in accordance with claim 1, wherein the intermediate element is in direct contact with the first and second necks.

21. The endoprosthesis for part of the pelvis in accordance with claim 1, wherein the first and second necks have ends which are opposite each other.

22. The endoprosthesis for part of the pelvis in accordance with claim 1, wherein the first and second necks are arranged opposite each other and the intermediate element is disposed between opposing ends of the first and second necks.

23. The endoprosthesis for part of the pelvis in accordance with claim 1, wherein the first neck projects from the base element towards the hip shell and the second neck projects from the hip shell towards the base element.

* * * * *